(12) United States Patent
Leland

(10) Patent No.: US 10,716,887 B2
(45) Date of Patent: Jul. 21, 2020

(54) FILTRATION MODULE

(71) Applicant: PDL BioPharma, Inc., Incline Village, NV (US)

(72) Inventor: Jonathan Leland, Gaithersburg, MD (US)

(73) Assignee: PDL BioPharma, Inc., Incline Village, NV (US)

( * ) Notice: Subject to any disclaimer, the term of this patent is extended or adjusted under 35 U.S.C. 154(b) by 194 days.

(21) Appl. No.: 16/024,889

(22) Filed: Jul. 1, 2018

(65) Prior Publication Data

US 2018/0369473 A1 Dec. 27, 2018

Related U.S. Application Data

(62) Division of application No. 14/361,733, filed as application No. PCT/US2012/067041 on Nov. 29, 2012, now Pat. No. 10,029,041.

(60) Provisional application No. 61/565,253, filed on Nov. 30, 2011.

(51) Int. Cl.
*A61M 1/34* (2006.01)
*B01D 61/18* (2006.01)
*B01D 63/08* (2006.01)
*G01N 33/49* (2006.01)

(52) U.S. Cl.
CPC .............. *A61M 1/34* (2013.01); *A61M 1/341* (2014.02); *B01D 61/18* (2013.01); *B01D 63/084* (2013.01); *G01N 33/491* (2013.01); *A61M 2205/75* (2013.01)

(58) Field of Classification Search
CPC .... A61M 1/34; A61M 1/341; A61M 2205/75; B01D 61/18; B01D 63/084; G01N 33/491
See application file for complete search history.

(56) References Cited

U.S. PATENT DOCUMENTS

2004/0245102 A1* 12/2004 Gilbert ................. B01D 63/087
 204/451
2006/0029923 A1* 2/2006 Togawa ................. B01D 61/18
 435/2

* cited by examiner

*Primary Examiner* — John Kim
(74) *Attorney, Agent, or Firm* — Finnegan, Henderson, Farabow, Garrett & Dunner LLP

(57) ABSTRACT

Provided is a filtration module for separating plasma from blood comprising a feeder channel lid, a feeder channel defined by a feeder channel laminating layer having a thickness of less than 5 mil, a filter element in fluid communication with the feeder channel and having a pore size of less than 2 microns and low surface area, and a filtrate take-off port having a dead volume of less than 10 µL. Also provided are methods for filtering a blood sample comprising supplying the blood sample to a feeder channel of a filtration module and drawing the blood sample over a filter element of the filtration module in a single pass process configuration to provide a retentate and a plasma filtrate.

9 Claims, 6 Drawing Sheets

FILTRATION MODULE

CROSS-REFERENCE TO RELATED APPLICATIONS

This application is a divisional application claiming the benefit under 35 U.S.C. 121 of U.S. patent application Ser. No. 14/361,733, filed on May 30, 2014, now U.S. Pat. No. 10,029,041, which is a national stage application under 35 U.S.C. 371 of International Application No. PCT/US2012/067041, filed internationally on Nov. 29, 2012, which claims priority to U.S. Provisional Patent Application No. 61/565,253, filed on Nov. 30, 2011, each of which is herein incorporated by reference in its entirety.

FIELD

The present disclosure relates to specimen preparation by filtration for clinical laboratory testing. In particular, a filtration module is disclosed that can be used in a filtration system.

BACKGROUND

The conventional preparation method for producing plasma from blood in a clinical laboratory is centrifugation. Disadvantages of centrifugation include equipment cost and complicated handling, especially at large scale. In order for filtration to be a viable alternative to centrifugation, the method must yield plasma that is of the same quality as that of centrifuged plasma, which generally means that filtered plasma must have the same composition as centrifuged plasma. Such quality is not achieved without careful consideration of the different forces acting upon blood between centrifugation and filtration. Blood is a complex biological fluid whose composition is highly dependent on methods of manipulation. Known to the clinical laboratory are unwanted composition changes that may occur such as red blood cell lysis, clotting, and loss of antigen if the separation is incorrectly conducted. Specifically, the analyte of interest in the plasma may be at different concentrations between centrifugation and filtration due to the loss of analyte to the filter by adsorption. The amount of material lost to the surface of a filter depends on the surface properties and surface area of the filter. Filter membranes are typically made of materials such as polymers and glass fibers that because of their surface properties adsorb components of the plasma. Additional composition changes may occur, which have potential adverse effects. The amount of red blood cell lysis caused by the filtration must be negligible. The filtration process should not induce the fibrinogen formation, i.e., clotting. These are all common pitfalls of filtration methods, and ones that must be avoided in order to successfully replace centrifugation.

The amount of blood available for a clinical laboratory analysis is that volume from a blood collection tube, which is typically about 2 mL to about 10 mL. In order to be a viable alternative to centrifugation, a filtration method must yield sufficient plasma for the clinical laboratory analysis. The maximum amount of plasma available from blood is the difference in total volume and hematocrit. For example, with 4 mL of blood from a patient with 40% hematocrit, the total amount of plasma is 2.4 mL. Typical of all filtration methods, the entire plasma content of blood is not recoverable. The amount of plasma collected relative to the total available plasma is the plasma recovery efficiency. For example, if 1.2 mL of plasma from the available 2.4 mL is collected, then the plasma recovery efficiency is 50%.

SUMMARY

The present disclosure provides a filtration module for separating plasma from blood including a feeder channel lid and a feeder channel defined by a feeder channel laminating layer having a thickness of less than about 5 mil; a filter element in fluid communication with the feeder channel and having a pore size of less than about 2 microns; and a ratio of actual surface area to projected surface area of less than about 5.0; and a filtrate take-off port having a dead volume of less than about 10 µL.

In some embodiments, the disclosure relates generally to a filtration module, wherein the filter element has a pore size of about 0.2 microns to about 1.0 microns.

In some embodiments, the disclosure relates generally to a filtration module, wherein the feeder channel laminating layer has a thickness of less than about 2 mil.

In some embodiments, the disclosure relates generally to a filtration module, wherein the feeder channel laminating layer has a thickness of about 0.9 mil to about 1.3 mil.

In some embodiments, the disclosure relates generally to a filtration module, wherein the filtrate take-off port has a dead volume of less than about 6 µL.

In some embodiments, the disclosure relates generally to a filtration module, wherein the filtrate take-off port has a dead volume of about 4.8 µL to about 5.2 µL.

In some embodiments, the disclosure relates generally to a filtration module, wherein the filtrate take-off port has a dead volume of less than or equal to about 2.9 µL per cm$^2$ of filtrate take-off port area.

In some embodiments, the disclosure relates generally to a filtration module, wherein the filtrate take-off port has a dead volume of less than or equal to about 2.5 µL per mL of blood filtered.

In some embodiments, the disclosure relates generally to a filtration module, wherein the filtration module has a thickness of about 4 mil to about 16 mil.

In some embodiments, the disclosure relates generally to a filtration module, wherein the filtration module has a length of about 1 inch to about 3 inches and a width of about 0.1 inch to about 1 inch.

The present disclosure further provides a filtration module for separating plasma from blood including a feeder channel lid; a feeder channel defined by a feeder channel laminating layer having a height of less than about 5 mil; a filter element in fluid communication with the feeder channel and having a pore size of less than about 2 microns; and an exposed area of less than or equal to about 0.6 cm$^2$ per mL of filtered blood; and a filtrate take-off port having a dead volume of less than about 10 µL.

In some embodiments, the disclosure relates generally to a filtration module, wherein the filtrate take-off port has a dead volume of less than or equal to about 2.5 µL per mL of blood filtered.

In some embodiments, the disclosure relates generally to a filtration module, wherein the filtrate take-off port has a dead volume of less than or equal to about 2.9 µL per cm$^2$ of filtrate take-off port area.

The present disclosure also provides a method for filtering a blood sample, the method including the steps of supplying the blood sample to a feeder channel of a filtration module; drawing the blood sample over a filter element of the filtration module in a single pass to provide a retentate and a plasma filtrate; and discarding the retentate or further processing the plasma filtrate.

The present disclosure further provides a method for filtering a blood sample, the method including the steps of supplying the blood sample to a feeder channel of a filtration module; and drawing the blood sample over a filter element of the filtration module in a single pass to provide a retentate and a plasma filtrate; where the method comprises a plasma recovery efficiency of greater than about 15%.

In some embodiments, the disclosure relates generally to methods for filtering a blood sample, wherein the filtration module further comprises a feeder channel lid; the feeder channel defined by a feeder channel laminating layer having a thickness of less than about 5 mil; the filter element in fluid communication with the feeder channel and having: a pore size of less than about 2 microns; and a ratio of actual surface area to projected surface area of less than or equal to about 5.0; and a filtrate take-off port having a dead volume of less than about 10 µL.

In some embodiments, the disclosure relates generally to methods for filtering a blood sample, wherein the filtration module further comprises a feeder channel lid; the feeder channel defined by a feeder channel laminating layer having a height of less than about 5 mil; the filter element in fluid communication with the feeder channel and having: a pore size of less than about 2 microns; and a filter element exposed area of less than or equal to about 0.6 cm$^2$ per mL of filtered blood; and a filtrate take-off port having a dead volume of less than about 10 µL.

In some embodiments, the disclosure relates generally to methods for filtering a blood sample, wherein the filtrate take-off port has a dead volume of less than or equal to about 2.5 µL per mL of blood filtered.

In some embodiments, the disclosure relates generally to methods for filtering a blood sample, wherein the filtrate take-off port has a dead volume of less than or equal to about 2.9 µL per cm$^2$ of filtrate take-off port area.

The present disclosure includes a number of other exemplary features such as those explained hereinafter. It is to be understood that the descriptions, examples, and figures disclosed herein are exemplary only.

BRIEF DESCRIPTION OF THE DRAWINGS

The accompanying tables and figures are incorporated in, and constitute a part of this specification.

DETAILED DESCRIPTION

Figure 1:
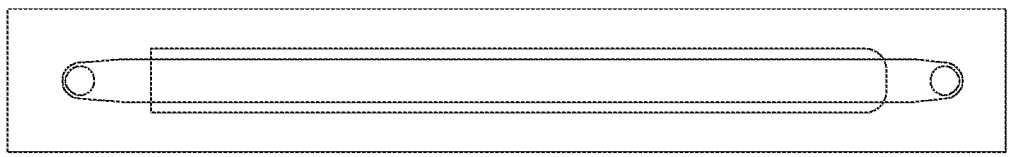
FIG. 1 is a top view of an exemplary embodiment of the presently disclosed filtration module.

Presently disclosed is a filtration module for sample preparation. The filtration module is arranged as a thin flatbed filtration cell. In an exemplary embodiment, the filtration module comprises four layers. It is contemplated that the filtration module can include more than four layers, such as, for example, five or six layers. A tangential flow filtration process is used to produce plasma of the necessary quality for sample preparation.

The presently disclosed filtration module, when assembled into a filtration system, provides for an economy in the number of filtration system support components. A filtration system is an assembly of components necessary to conduct a filtration (see, for example, FIG. 7). A filtration module is one component of a filtration system. Other system components which support the operation of the filtration module may include pumps, valves, sensors, controllers, fittings, adapters, manifolds, mounting brackets, conduits, tubing, waste reservoirs, and product collection vessels. An economy in the number of required system support components is beneficial because of lower costs and increased reliability.

The presently disclosed filtration module is operable in a single pass process configuration. A single pass process configuration is advantageous compared to reciprocated flow and re-circulated flow process configurations. A single pass process configuration is an optimal choice when processing blood as part of the sample preparation for a clinical laboratory analysis. High filtration efficiency and performance are achieved with only a single pass of blood through the filtration module. Because of this, the single pass process configuration avoids blood from passing through the pump as would be commonly employed with re-circulating flow process configuration. The single pass process configuration avoids the need to repeatedly disconnect and reconnect the pump as would be the situation for reciprocated flow process configuration.

The presently disclosed filtration module is a tangential flow filtration module. Tangential flow filtration is advantageous for filtering liquids, such as blood, which contain a high proportion of small size particles. With sufficiently high wall shear, tangential flow filtration modules operate at high efficiency. Tangential flow filtration modules avoid the use of high surface area filter elements common with dead stop filtration.

The filtration module of the present disclosure is comprised of a low surface area filter element. The filter element has a pore size large enough to allow passage of substantially all the blood constituents except red blood cells. The filtration module is further comprised of a thin feeder channel laminating layer. The feeder channel is very thin so as to produce the high wall shear rates necessary with tangential flow filtration to yield high filtration efficiencies (e.g., high plasma recovery efficiencies). The filtration module is further comprised of a low dead volume filtrate take-off port. A low dead volume take-off maximizes the plasma recovery efficiency, which is necessary when the available blood volumes are limited. The filtration module is further comprised of a thin feeder channel lid. When the filtration module is assembled, a thin and compact device is formed.

The presently disclosed filtration module provides certain advantages when assembled into a filtration system, including, for example, that it is automatable. Automated operation is beneficial because of lower costs and increased reliability. Another advantage is that the presently disclosed filtration module rapidly filters blood into plasma. Additionally, the filtration module of the present disclosure, when manufactured, is low cost. Consequently, a filtration module may be discarded after a single use because of the low cost. A low cost filtration module avoids the need to re-generate or re-clean the filtration module, and avoid possible cases of contamination.

The presently disclosed filtration module is used to prepare blood specimens as part of a clinical laboratory analysis. The filtration module produces filtered plasma of suitable quality for a clinical laboratory analysis and is operable on low volumes of blood.

The presently disclosed filtration module is small and compact. Advantageously, the filtration module is adaptable in several ways. The filtration module is adaptable for either one- or two-side mounting to a filtration system. The filtration module is further adaptable to different available blood volumes. These adaptations will be evident through various embodiments of the presently disclosed filtration module.

Definitions

The following terms or phrases used in the present disclosure have the meanings outlined below:

"Feeder channel" is intended to mean the volume adjacent to and on the retentate side of a filter element in a filtration module, through which the sample to be filtered passes.

"Feeder channel laminating layer" refers to a layer of material adjacent and on the retentate side of a filter element in a filtration module. The feeder channel laminating layer defines the area and height (or thickness), and thus the volume, of the feeder channel. In an embodiment, an interior cutout of feeder channel laminating layer defines the area of the feeder channel. Further details about the laminating material chosen for the feeder channel laminating layer are provided below.

"Feeder channel lid" refers to a layer of material adjacent the feeder channel laminating layer (and opposite the filter element layer), which encloses the sample to be filtered within the feeder channel.

"Filter element" or "filter element layer" refers to the layer of material through which the sample is filtered. The filter element has a filtrate side and a retentate side. Further details about the material chosen for the filter element are provided below.

"Filtrate side" refers to the face of the filter element where sample which is smaller than the pore size flows. Substances smaller than the pore size pass from the retentate side through the filter element to the filtrate side. The filtrate side is the face opposite the retentate side.

"Filtrate take-off port" is intended to mean the volume adjacent to and on the filtrate side of a filter element in a filtration module, from which filtrate is recovered.

"Filtrate take-off layer" refers to a layer of material adjacent and on the filtrate side of a filter element in a filtration module. The filtrate take-off layer defines the area and height (or thickness), and thus the volume, of the filtrate take-off port. In an embodiment, an interior cutout of filtrate take-off layer defines the area of the filtrate take-off port.

"Inlet port" refers to an opening in a layer of the filtration module through which the sample to be filtered enters the filtration module. For example, the inlet port may be an opening in the filtrate take-off layer or the feeder channel lid layer.

"Inlet via" refers to a through hole in a layer of the filtration module that connects the inlet port with the feeder channel. For example, the inlet via may be a through hole in the filter element layer.

"Laminating element" refers to a thin material used to join or bond materials together. A laminating element typically uses adhesive as the means to hold together materials in layers. For example, a laminating element may be a pressure sensitive adhesive tape or thermal adhesive film.

"Retentate outlet port" refers to an opening in a layer of the filtration module through which filtration retentate can be removed or recovered from the filtration module. For example, the retentate outlet port may be an opening in the filtrate take-off layer or the feeder channel lid layer.

"Retentate outlet via" refers to a through hole in a layer of the filtration module that connects the retentate outlet port with the feeder channel. For example, the retentate outlet via may be a through hole in the filter element layer.

"Retentate side" refers to the face of the filter element where sample larger than the pore size flows. Substances larger than the pore size do not pass through the filter element and are retained on the retentate side of the filter element. The retentate side is the face opposite the filtrate side.

The present disclosure relates to a filtration module that can be used in a filtration system. In particular, the filtration module is useful for separating plasma from blood. In several exemplary embodiments the filtration module of the present disclosure can include a feeder channel lid and a feeder channel defined by a feeder channel laminating layer having a thickness of less than about 5 mil. The filtration module can further include a filter element in fluid communication with the feeder channel and having a pore size of less than about 2 microns, and a ratio of actual surface area to projected surface area of less than or equal to about 5.0. The filtration module of the present disclosure can also include a filtrate take-off port having a dead volume of less than about 10 μL.

Figure 2:
FIG. 2 is a side view of an exemplary embodiment of the presently disclosed filtration module.
Figure 3:
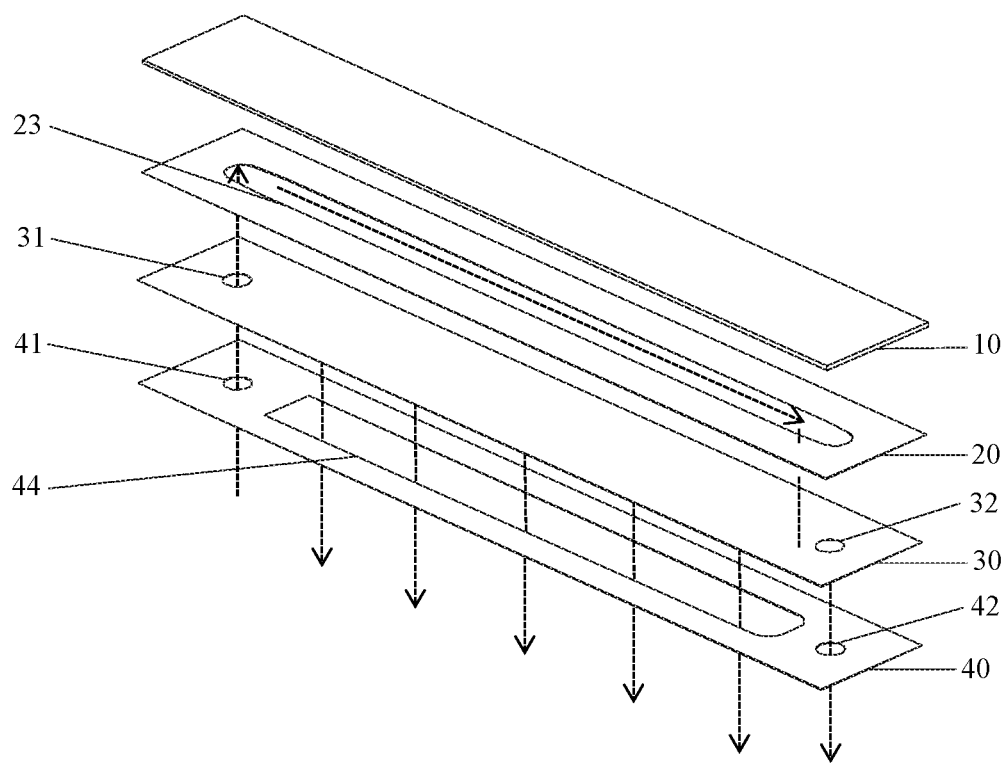
FIG. 3 is an expanded perspective view of an exemplary embodiment of the presently disclosed filtration module, with arrows showing a flow path through the filtration module.

An exemplary embodiment of the presently disclosed filtration module is depicted in FIGS. 1-3. FIG. 1 shows a top view, FIG. 2 shows a side view, and FIG. 3 shows an exploded perspective view of an exemplary embodiment of a filtration module adapted for one-side mounting. In particular, FIG. 3 shows an exemplary embodiment of a four-layered filtration module including a feeder channel lid layer 10, a feeder channel laminating layer 20, a filter element layer 30, and a filtrate take-off layer 40.

In an exemplary embodiment of a filtration module adapted for one-side mounting, an inlet port 41, a filtrate take-off port 44, and a retentate outlet port 42 are formed out of the filtrate take-off layer 40. The filtration module adapted for one-side mounting can further include the filter element layer 30 with an inlet via 31 and a retentate outlet via 32. The inlet port 41 and retentate outlet port 42 of the filtrate take-off layer 40 correspond with the inlet via 31 and the retentate outlet via 32 of the filter element layer 30. The filtrate take-off layer 40 is joined to the filtrate side of the filter element layer 30. One-side mounting to the filtration system minimizes connecting elements to the filtration system.

The filter element layer 30 is essential to the filtration module as it is the primary layer for separating red blood cells from plasma. For the presently disclosed filtration module, the filter element layer 30 is selected for particularly sized pores, which allow passage of the main constituents of blood while retaining red blood cells. Red blood cells are flexible biconcave disks with disk diameter of about 6 microns to about 8 microns and with typical thickness of about 2 microns. Because red blood cells are deformable, the largest possible pore size must be smaller than the smallest dimension of the cell. For optimal blood filtration, the pore size is recommended to be less than 2 microns, for example, from about 0.2 to about 1.0 microns.

The filter element layer 30 of the presently disclosed filtration module has a low surface area of the filter element layer 30 exposed to blood, referred to as a filter element exposed area. The amount of analyte lost to the filter surface by adsorption depends on the filter element exposed area. If the area of the filter is sufficiently small, then the amount of analyte lost is negligible. The filter element exposed area is a product of the geometric area of a feeder channel 23 formed out of the feeder channel laminating layer 20 and a surface roughness parameter. The surface roughness parameter, as used herein, is the ratio of actual surface area to projected surface area and it is a characteristic of the material chosen for the filter element layer 30. The actual surface area, as used herein, is a measure of the microscopic area available for adsorption of analyte. The projected surface area, as used herein, is the geometric area of the feeder channel.

In an exemplary embodiment of the filtration module, the filter element layer 30 can be made of a material whose actual surface area is substantially the same as the projected surface area. (i.e., a material with low surface roughness parameter). Using such a filter element layer 30 along with an optimally sized area of the feeder channel 23, minimizes the filter element exposed area, which avoids filtered plasma quality not being equivalent to centrifuged plasma through losses of analyte to the filter surface. An optimally sized area of the feeder channel refers to a size that improves filtered plasma quality. For example, the amount of analyte lost to the filter surface by adsorption depends on the filter element exposed area. Thus, if the area of the filter is sufficiently small, such as, for example, about 1.2 cm$^2$, then the amount of analyte lost is negligible. For the presently disclosed filtration module, the filter element layer 30 has a ratio of actual surface area to projected surface area of less than or equal to about 5.0, for example, less than or equal to about 1.1.

The presently disclosed filtration module is designed to have a thin filter element layer 30. An example of a suitable material to use for the filter element 30 is Whatman Cyclopore™ 0.6 micron pore size polycarbonate tracked etched filter membranes with a thickness of about 0.8 mil. The filter element layer 30 is chemically inert and exhibits very low levels of extractables. It is desirable to have pores of the filter element layer 30 that are cylindrical through holes with tightly controlled diameter and with near unity pore size distribution.

An exemplary embodiment of the filtration module of the present disclosure can have the filtration module arranged as a flat bed, where the filter element layer 30 may be rectangular or square in shape. It is contemplated that other arrangements may be used such as spiral wound modules. In another exemplary embodiment, the filter element layer 30 can have a length of about 1 inch to about 3 inches, for example, about 2.4 inches or about 2.6 inches, and a width of about 0.1 inch to about 1 inches, for example, about 0.34 inches or about 0.5 inches.

Overall, the feeder channel 23 is critical to the proper operation of a filtration module for tangential flow filtration. As shown in FIG. 3, the feeder channel 23 is further defined and formed by joining a feeder channel laminating layer 20 and a feeder channel lid layer 10 to the retentate side of the filter element layer 30. The feeder channel laminating layer 20 is the primary layer that defines the characteristics of the feeder channel 23, such as the filter element exposed area and the height of the feeder channel 23.

In certain embodiments, the feeder channel laminating layer 20 is selected to be fluidically thin. Thus, examples of suitable materials from which the feeder channel laminating layer 20 can be constructed include, but are not limited to, 3M™ Double Coated Tape 9019, Adhesive Applications HRFP025, Specialty Tapes D100, or Adhesives Research ARcare 8570. The height or thickness of the feeder channel laminating layer 20 defines the height of the feeder channel 23. The height of the feeder channel 23 is an important feature for achieving high plasma recovery efficiency. For tangential flow filtration to operate at high efficiency, it is necessary that a high wall shear rate is capable of developing during the filtration process. High wall shear prevents filter fouling, which is especially relevant and crucial when filtering high solid content fluids such as blood. Exemplary embodiments of the presently disclosed filtration module incorporate a thin height of the feeder channel 23 of, for example, less than about 5 mil, less than about 2 mil, about 0.9 mil to about 1.3 mil, or about 1.1 mil. A thin channel for a tangential flow filtration flatbed filter cell is a necessary feature for filtering difficult liquids such as blood. In contrast, conventional tangential flow filtration flatbed filter cells typically use feeder channel heights of about 5 mil to about 20 mil. The wall shear rate for a rectangular feeder channel is given by equation 1 (Eq. 1):

$$\text{Wall shear rate} = \frac{6 \times Q}{(\text{channel width} \times \text{height}^2)} \qquad \text{Eq. 1}$$

where Q is volume flow rate

In another exemplary embodiment of the filtration module of the present disclosure, the channel width can be about 0.10 inch. As shown in Eq. 1, the wall shear rate is particularly sensitive to the channel height through a squared relationship. A thin height of the feeder channel increases wall shear. For example, decreasing the height of the feeder channel from about 5 mil to about 1.1 mil increases the wall shear rate by over 20 times.

For a rectangular channel, the relationship between Q and pressure is represented by equation 2 (Eq. 2):

$$P = \frac{12 \times V \times Q \times L}{(\text{channel width} \times \text{height}^3)} \qquad \text{Eq. 2}$$

where P is pressure, V is viscosity, L is channel length

By way of example only, in a situation with an applied pressure of 4 PSI, the blood flow rate would be 0.7 μL/s and the wall shear rate would be 2140 sec$^{-1}$.

In certain embodiments, the area of the feeder channel 23 is designed to be small. Minimizing the area of feeder channel 23 improves filtered plasma quality. The amount of analyte lost to the filter surface by adsorption depends on the filter element exposed area. If the area of the filter is sufficiently small, then the amount of analyte lost is negligible. In an exemplary embodiment, the area of the feeder channel 23 can be, for example, about 1.2 cm$^2$. It is contemplated that the area of the feeder channel 23 can be adjusted and adapted to the overall design of the filtration module and for the targeted filtrate/filtered substance.

The amount of analyte lost to the filter surface by adsorption also depends on the volume of blood passed through the feeder channel 23. In an exemplary embodiment, the operable blood volume can be, for example, greater than or equal to about 2 mL. It is contemplated that the operable blood volume of the filtration module can be adjusted and adapted to the overall design of the filtration module and the targeted filtrate/filtered substance. For example, the operable blood volume can be greater than or equal to about 1.5 mL, or greater than or equal to about 1.0 mL.

The feeder channel laminating layer 20 is selected to be a laminating element, such as a double-sided pressure sensitive adhesive tape. A suitable example of double-sided pressure sensitive adhesive tape is 3M™ Double Coated Tape 9019 with nominal thickness of about 1.1 mil. The use a laminating element to construct the feeder channel laminating layer 20 minimizes the height of the feeder channel 23 by eliminating the need to use an addition spacer to define the height. Thus, in certain embodiments, the construction of the filtration module is configured to avoid extra and unwanted channel height, which increases wall shear rate and plasma recovery efficiency. In certain other embodiments of the filtration module, the use of pressure sensitive adhesive tape also ensures uniformity in the height of the feeder channel 23 and at low cost.

As shown in FIG. 3, the exemplary embodiment of the filtration module of the present disclosure is further comprised of a feeder channel lid layer 10, which is joined to the feeder channel laminating layer 20 using the adhesive face of feeder channel laminating layer 20 acting as a laminating element. The feeder channel lid layer 10, when joined with the feeder channel laminating layer 20, further defines and encloses the feeder channel 23.

The feeder channel lid layer 10 can be made from a variety of materials that provide any or all of several desired properties. For example, it is desirable to have a thin feeder channel lid layer 10 that is dimensionally stable under high pressure or vacuum. In particular, the thin property is desirable to make the filtration module overall small and compact. It is also advantageous and desirable to use a material that is chemically inert and has sufficient adhesion to the laminating element, such as feeder channel laminating layer 20. In certain embodiments, the feeder channel lid layer 10 optionally may be optically transparent. An example of a suitable material to use as the feeder channel lid layer 10 is DuPont Melinex® 561 Polyester film with a thickness of 10 mil. It is contemplated that other commercially available materials can be used as the feeder channel lid layer 10, such as, for example, Questar™ 1000 gauge polyester film, or Dura-lar 0.010 inch PET film.

The exemplary embodiment of the filtration module shown in FIG. 3 further includes a filtrate take-off layer 40, which is joined to a filtrate side (opposite of a retentate side) of the filter element layer 30. The filtrate take-off layer 40 can be composed of a laminating element such as, for example, a double-sided pressure sensitive adhesive tape. It is desirable to select a material for the filtrate take-off layer 40 that is thin, uniform, and low cost. An example of a suitable material to use as the filtrate take-off layer 40 is 3M™ Double Coated Tape 9019 with a nominal thickness of about 1.1 mil. The use of a laminating element for the filtrate take-off layer 40 allows for joining and sealing the filter element layer 30 to the filtration system with one layer, thus minimizing overall thickness and height by avoiding use of additional spacers or layers.

In exemplary embodiments of the presently disclosed filtration module, the filtrate take-off layer 40 features a low dead volume filtrate take-off port 44. The dead volume is determined by the product of laminating element thickness and the area of the filtrate take-off port 44. The use of a thin laminating element to form the filtrate take-off port 44 lowers dead volume on the filtrate side of the filter element layer 30. A low dead volume filtrate take-off port 44 maximizes the plasma recovery efficiency, which is necessary when the available blood volumes are limited. In an exemplary embodiment of the presently disclosed filtration module the dead volume can be, for example, less than about 10 µL, less than about 6 µL, or from about 4.8 µL to about 5.2 µL. By way illustration, in an embodiment where the filtrate take-off port 44 has an area of 1.7 cm², the dead volume will be about 5 µL.

The filtrate take-off port area 44 is directly correlated and sized according to the geometric area of a feeder channel 23. The take-off port area and geometric area of a feeder channel 23 are nearly the same except for an oversizing of the filtrate take-off port width relative to the feeder channel by about 5 to about 30%.

Certain embodiments of the presently disclosed filtration module can have a typical overall thickness of about 4 mil to about 16 mil, such as, for example, from about 10 mil to about 16 mil, or about 12 mil, or about 13 mil. All layers of the filtration module can have the same length and width. However, it is contemplated that the size and area, including length and width, of each layer may be adjusted as needed if, for example, the filtration module is used in combination with or as part of an additional component such as a filtration system. The layers of the filtration module may be joined by a roll to roll laminating press. The features may be die cut or laser cut. It is contemplated that other methods of joining the layers may be used depending on the methods of manufacturing and materials used for the layers. Additionally, other methods of forming the layers may be employed based on manufacturing and cost goals and needs.

In the exemplary embodiment shown in FIG. 3, the flow path that a sample may travel within the filtration module (indicated by the arrows) would begin by entering through the inlet port 41 of the filtrate take-off layer 40, passing through the inlet via 31 of the filter element layer 30 to reach the feeder channel 23 of the feeder channel laminating layer 20. The sample flows into and along the feeder channel 23, the volume of which is defined in part by the feeder channel lid layer 10 and the filter element layer 30. The filtrate portion of the sample flows perpendicular to the filter element layer 30 and reaches the filtrate take-off port 44 of the filtrate take-off layer 40. The retentate portion of the sample flows parallel to the filter element layer 30 and exits through the retentate outlet via 32 of the filter element layer 30 and finally through the retentate outlet port 42 of the filtrate take-off layer 40. The filtrate can be collected or further transported and/or processed in a filtration system.

Figure 4:
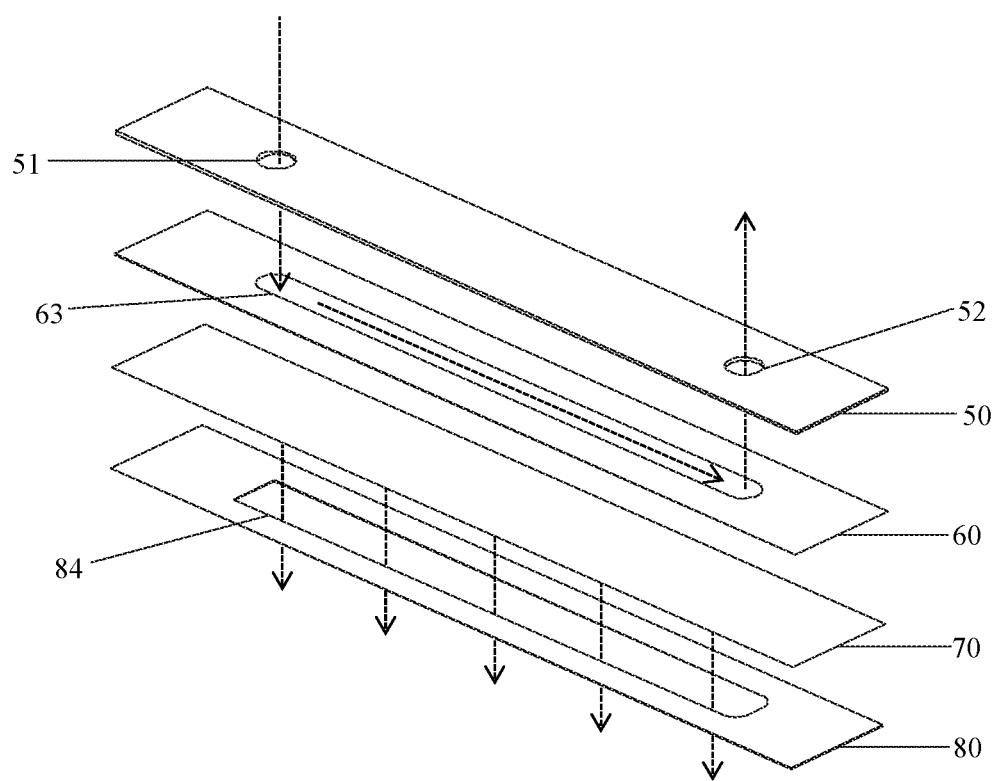
FIG. 4 is an expanded perspective view of an exemplary embodiment of the presently disclosed filtration module, with arrows showing a flow path through the filtration module.

Another exemplary embodiment of the presently disclosed filtration module is shown in FIG. 4. FIG. 4 provides an exploded perspective view of an exemplary embodiment of a four-layered filtration module adapted for two-side mounting to the filtration system. The exemplary embodiment of the filtration module depicted in FIG. 4 is adapted for two-side mounting as an inlet port 51 and a retentate outlet port 52 are on a same first surface or the retentate side of a feeder channel lid layer 50 and a filtrate take-off port 84 is on an opposite and corresponding surface or the filtrate side of a filtrate take-off layer 80. Two-side mounting can be advantageous when a product collection vessel is separate from the source and waste.

The feeder channel lid layer 50 can be constructed from various materials that exhibit some stiffness, are dimensionally stable under high pressure or vacuum, and can be joined to another surface such as a single-sided tape. It is also advantageous and desirable to use a material that is chemically inert and has sufficient adhesion to a laminating element, such as a feeder channel laminating layer 60. In certain embodiments, the feeder channel lid layer 50 optionally may be optically transparent. Thus, examples of suitable materials from which the feeder channel lid layer 50 can be constructed include Adhesive Applications A702, Specialty Tapes S504, or Adhesives Research ARcare 8565. The adhesive face of single-sided tape is used to join the filtration module of the present disclosure to the filtration system.

An additional layer, a feeder channel laminating layer 60, can be constructed from various materials that are fluidically thin, such as, for example, a laminating element. Thus, examples of suitable materials from which the feeder channel laminating layer 60 can be constructed include a double-sided pressure sensitive adhesive tape, 3M™ Double Coated Tape 9019, Adhesive Applications HRFP025, Specialty Tapes D100, or Adhesives Research ARcare 8570. A feeder channel 63, formed from and defined by the feeder channel laminating layer 60, when joined to a filter element layer 70, features a low filter element exposed area. As previously discussed, a low filter element exposed area refers to sufficiently small filter element exposed area such that the amount of analyte lost by adsorption to the filter surface is negligible. The exemplary embodiment of the filtration module is designed to have a thin filter element layer 70. An example of a suitable material to use for the filter element 70 is Whatman Cyclopore™ 0.6 micron pore size polycarbonate tracked etched filter membranes with a thickness of about 0.8 mil. The filter element layer 70 is chemically inert and exhibits very low levels of extractables. It is desirable to have pores of the filter element layer 70 that are cylindrical through holes with tightly controlled diameter and with near unity pore size distribution.

In another exemplary embodiment for mounting, the inlet port 51 is on the same side as the filtrate take-off port 84 and the retentate outlet port 52 is on the opposite side. In still another exemplary embodiment for mounting, the retentate outlet port 52 is on the same side as the filtrate take-off port 84, while the inlet port 51 is on the opposite side.

Certain exemplary embodiments of the presently disclosed filtration module can be adapted by scaling certain features that depend on the minimum operable blood volume of the filtration module, which is the minimum volume of blood necessary to pass through the feeder channel 63 so as to yield plasma of quality substantially the same as centrifuged plasma. The minimum operable blood volume depends on the filter element exposed area. The amount of analyte lost to the filter surface by adsorption depends on the filter element exposed area. If the filter element exposed area is sufficiently small relative to the volume passed through the feeder channel 63, then the amount of analyte lost is negligible. Establishing a maximum filter element exposed area relative to the available blood volume improves filtered plasma quality.

In a further embodiment of the presently disclosed filtration module, the maximum filter element exposed area depends on the available blood volume. The amount of analyte lost scales proportionally with the filter area. For a given volume of blood to be filtered, the filter element exposed area should be small enough that the amount of analyte lost to the filter surface by adsorption is negligible. For example, the filter element exposed area may be less than or equal to about 0.6 $cm^2$ per mL of blood.

In still another embodiment of the presently disclosed filtration module, the minimum operable blood volume of the filtration module scales with the filter element exposed area. For a given filter area, for example, the minimum operable blood volume of the filtration module may be greater than or equal to about 1.7 mL of blood per $cm^2$ of filter area.

Other exemplary embodiments of the presently disclosed filtration module can be further adapted by scaling certain features, which minimize unwanted dead volume. The dead volume of the filtration module is unwanted as it lowers plasma recovery efficiency. As used herein and with reference to the filtration module of the present disclosure, "dead volume" is intended to mean the volume of plasma trapped within the filtrate take-off port, which is unrecoverable. Upon completion of the filtration process, which is after the passing of the available blood volume through the feeder channel, any plasma not transported to the filtration system collection vessel is dead volume. That portion of the plasma confined to the filtrate take-off port is the relevant dead volume of the filtration module. The actual dead volume of the filtration module is the product of the filtrate take-off port area and thickness of the filtrate take-off layer.

In certain embodiments of the presently disclosed filtration module, a thin filtrate take-off layer 80 is incorporated into the design of the filtration module for the purpose of minimizing filtration module dead volume. The thickness of the filtrate take-off layer may be less than or equal to about 5 mil. The filtrate take off layer 80 can be constructed from various materials that are fluidically thin, such as, for example, a laminating element. Thus, examples of suitable materials from which the filtrate take off layer 80 can be constructed include a double-sided pressure sensitive adhesive tape, such as 3M™ Double Coated Tape 9019, Adhesive Applications HRFP025, Specialty Tapes D100, or Adhesives Research ARcare 8570. It is contemplated that the filtrate take-off layer 80 may be the same material as the feeder channel laminating layer 60.

The filtrate take-off port area 84 is directly correlated and sized according to the geometric area of a feeder channel 63. The take-off port area and geometric area of a feeder channel 63 are nearly the same except for an oversizing of the filtrate take-off port width relative to the feeder channel by about 5 to about 30%.

In certain embodiments of the presently disclosed filtration module, the filtration module dead volume can scale with the filtrate take-off port area. For example, the filtration module dead volume may be less than or equal to about 2.9 µL per $cm^2$ of filtrate take-off port area.

In certain embodiments of the presently disclosed filtration module, the filtration module dead volume can scale with the minimum operable blood volume. For example, the filtration module dead volume may be less than or equal to about 2.5 µL per mL of blood.

In the exemplary embodiment shown in FIG. 4, the flow path that a sample may travel within the filtration module (indicated by the arrows) would begin by entering through the inlet port 51 of the feeder channel lid layer 50. The sample flows into and along the feeder channel 63 of the feeder channel laminating layer 60, the volume of which is defined in part by the feeder channel lid layer 50 and the filter element layer 70. The filtrate portion of the sample flows perpendicular to the filter element layer 70 and reaches the filtrate take-off port 84 of the filtrate take-off layer 80. The retentate portion of the sample flows parallel to the filter element layer 70 and exits through the retentate outlet port 52 of the feeder channel lid layer 50. The filtrate can be collected or further transported and/or processed in a filtration system.

Figure 5:
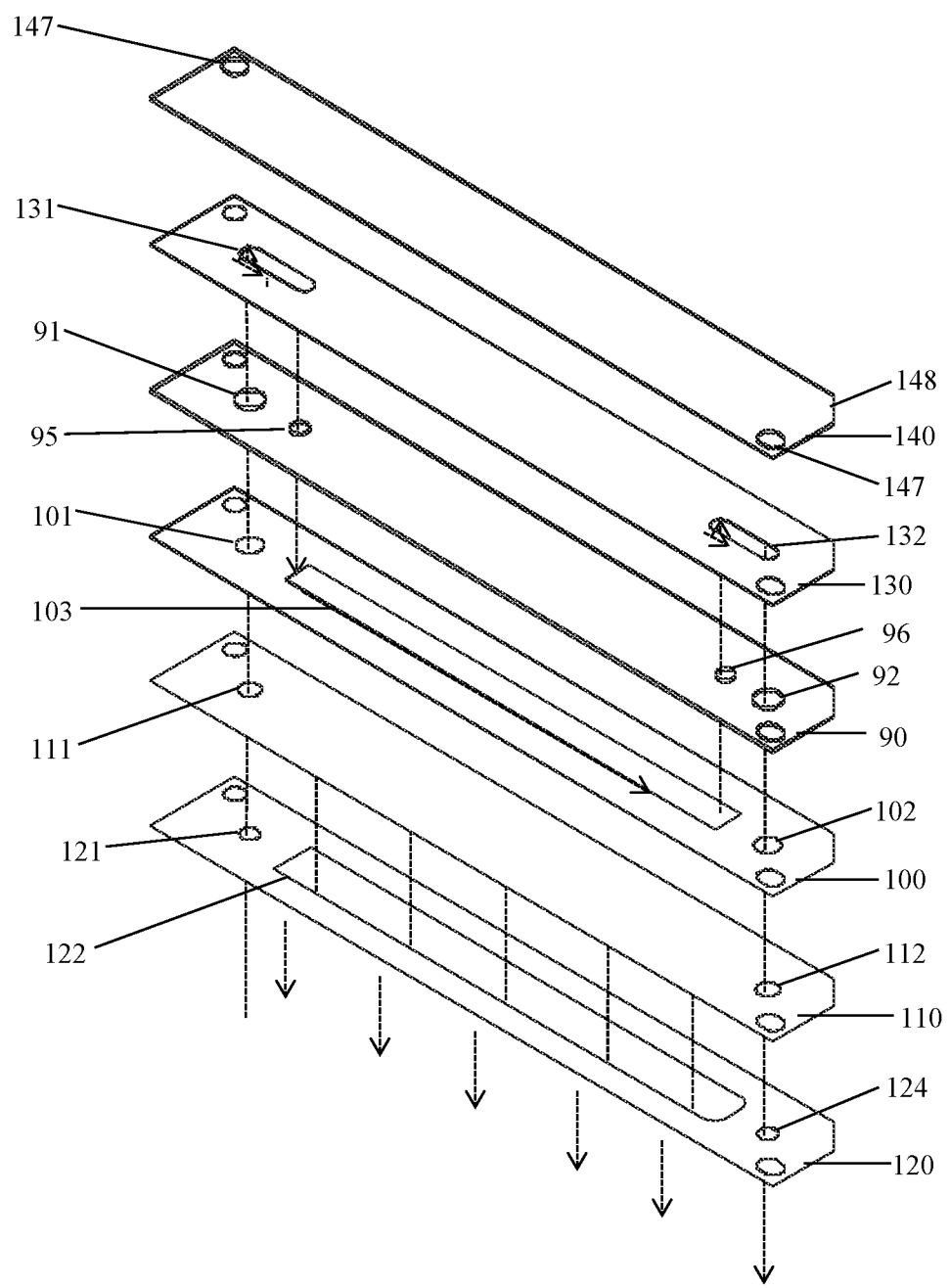
FIG. 5 is an expanded perspective view of an exemplary embodiment of the presently disclosed filtration module, with arrows showing a flow path through the filtration module.

An exemplary embodiment of the presently disclosed filtration module is shown in FIG. 5. The filtration module of FIG. 5 can be formed from six layers, as it has two additional layers relative to the four layer filtration module shown in FIG. 4. Shown in FIG. 5 are a feeder channel lid layer 90, a feeder channel laminating layer 100, a filter element layer 110, and a filtrate take-off layer 120, which are common to the layers of the filtration module in FIG. 4. A filtrate take off port 122 is formed out of the filtrate take off layer 120. The filtration module of FIG. 5 additionally includes a support layer 140 to provide more stiffness to the filtration module. Support layer 140 can be made from, for example, DuPont Melinex® 561 Polyester film with about 0.010 inch thickness. Examples of other suitable materials from which the support layer can be constructed include, but are not limited to, Questar™ 1000 gauge polyester film, or Dura-lar 0.010 inch PET film. Support layer 140 is joined to the feeder channel lid layer 90 using a laminating element 130, made from, for example, 3M™ Transparent Polyethylene Double Coated Medical Tape 1509 with 4.9 mil thickness. Examples of other suitable materials from which the laminating element can be constructed include a double-sided pressure sensitive adhesive tape 3M™ Double Coated Tape 9019, Adhesive Applications HRFP025, Specialty Tapes D100, or Adhesives Research ARcare 8570.

Laminating element 130 has two secondary channels 131, 132, which are slots formed in the layer that provide a fluidic path for an inlet via 91 and outlet via 92 to the feeder channel 103. Secondary channels 131, 132 add height (i.e., the height of the laminating element 130) to the entry and exit of the feeder channel 103, aiding fluid entry and exit through the feeder channel 103 and reducing pressure gradients at the entry and exit of the feeder channel 103. Feeder channel lid layer 90 is adapted to connect the secondary channels 131, 132 to the feeder channel 103 with inlet via 95 and outlet via 96. Support layer 140 also acts as a lid to the secondary channels 131, 132 in laminating element 130. It is important that the layers fit tightly together and are able to resist bulging during filtration. Thus, the presently disclosed embodiments of the filtration module are designed to promote tension throughout the layers when joined to form the filtration module. The filtration module as shown in FIG. 5 is adapted for one-side mounting to the filtration system. Each of the layers has at least two through holes 147 to facilitate alignment and a notched corner 148 to facilitate orientation of the filter to the filtration system. It is contemplated that additional through holes may be added to the filtration module as necessary to configure to any medical device within which it may be used. Likewise, it is contemplated that additional notches or altered shapes and sizes of the layers may be used in the design of the filtration module to adapt to any component, such as a medical device within which it may be used.

In the exemplary embodiment shown in FIG. 5, the flow path that a sample may travel within the filtration module (indicated by the arrows) would begin by entering through the inlet port 121 of the filtrate take-off layer 120, passing through the inlet via 111 of the filter element layer 110, further passing through inlet via 101 of the feeder channel laminating layer 100, further passing through inlet via 91 of the feeder channel lid layer 90 to secondary channel 131 of the laminating element layer 130.

The sample then passes along secondary channel 131 of the laminating element layer 130 and then further passes to the inlet via 95 of the feeder channel lid layer 90 to reach the feeder channel 103 of the feeder channel laminating layer 100. The sample flows along the feeder channel 103, the volume of which is defined in part by the feeder channel lid layer 90 and the filter element layer 110. The filtrate portion of the sample flows perpendicular to the filter element layer 110 and reaches the filtrate take-off port 122 of the filtrate take-off layer 120. The retentate portion of the sample flows parallel to the filter element layer 110 and exits through the retentate outlet via 96 of the feeder channel lid layer 90. The retentate further passes through to the secondary channel 132 of the laminating element layer 130. The retentate travels along the secondary channel 132 and passes through the outlet via 92 of the feeder channel lid layer 90. The retentate passes through the outlet via 102 of the feeder channel laminating layer 100, further passes through outlet via 112 of filter element layer 110, and finally through the retentate outlet port 124 of the filtrate take-off layer 120. The filtrate can be collected or further transported and/or processed in a filtration system.

As will be further demonstrated in the Examples, an exemplary embodiment of the presently disclosed filtration module performs with high plasma recovery efficiency (e.g., greater than 15%, greater than 25%, or greater than 35%), which is advantageous when the available blood is limited, such as with clinical laboratory specimens. Further, the high plasma recovery efficiency enables the filtration module to operate as a single pass process configuration. A single pass process configuration is an optimal choice because of an economy in the number of system components. Single pass process configurations are readily and efficiently automated. Additionally, a single pass process configuration avoids blood from passing through the pump as would be commonly employed with re-circulating flow process configuration. A single pass process configuration avoids the need to repeatedly disconnect and reconnect the pump as would be the situation for reciprocated flow process configuration.

While the various embodiments of the presently disclosed filtration module discussed herein enable the use of a single pass process configuration, the filtration module is operable with other process configurations such as re-circulated flow or reciprocated flow.

In an exemplary embodiment of the present disclosure, a method for filtering a blood sample is provided, the method comprising supplying the blood sample to a feeder channel of a filtration module, drawing the blood sample over a filter element of the filtration module in a single pass to provide a retentate and a plasma filtrate, and discarding the retentate or further processing the plasma filtrate. A pump may be used to facilitate the flow of the sample through the filtration module.

In another exemplary embodiment of the present disclosure, a method for filtering a blood sample is provided, the method comprising supplying the blood sample to a feeder channel of a filtration module and drawing the blood sample over a filter element of the filtration module in a single pass to provide a retentate and a plasma filtrate. The method can result in a plasma recovery efficiency of >15%.

Figure 7:
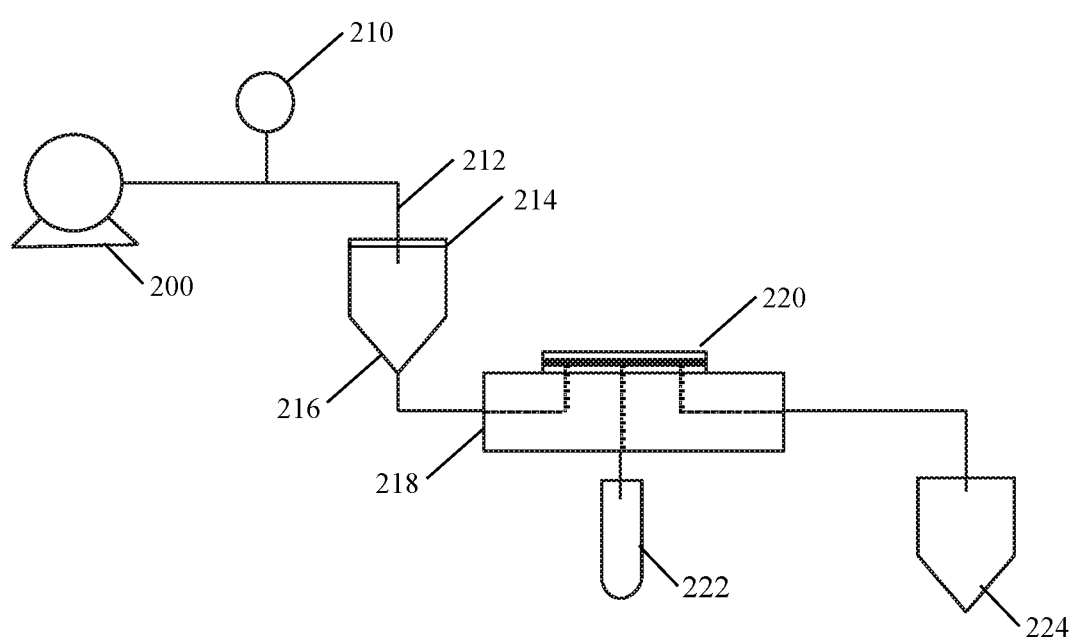
FIG. 7 is a schematic illustration of a filtration system incorporating an exemplary embodiment of the presently disclosed filtration module.

In another exemplary embodiment, the filtration module of the present disclosure can be used within a filtration system, such as that shown in FIG. 7. The filtration system may include a pump 200 and a pressure sensor 210. The pressure sensor 210 can gauge the magnitude of the pressure supplied by the pump 200. The pump 200 can be further connected to an input reservoir 216 through a probe 212 that can pierce and traverse a septum 214 on the input reservoir 216. The input reservoir 216 receives the sample by, for example, a pipette. The input reservoir 216 is closed using the septum 214. The input reservoir 216 receives constant air pressure from the pump 200 through the probe 212. Pressurization of the input reservoir 216 with air forces blood to flow to a manifold 218. The manifold 218 mounts to a filtration module 220, such as those exemplary embodiments of the present disclosure. The filtration module 220 receives sample through connecting lines within the manifold 218. The filtered sample can be collected in a collection tube 222 that may be positioned on the underside of the manifold 218 to receive the desired filtrate such as plasma. Any waste 224 may be collected and discarded. It is contemplated that many other configurations of filtration systems may be used with the filtration module of the present disclosure and the system described herein is for illustrative purposes only.

The following examples are merely illustrative and intended to be non-limiting.

EXAMPLES

Example 1

Comparison of Plasma Recovery Efficiency Between EDTA and Lithium Heparin Preserved Blood Plasma recovery efficiency was compared between blood preserved with two different anti-coagulants, potassium EDTA (ethylenediaminetetraacetic acid) and lithium heparin.

Whole human blood was obtained from normal healthy volunteers. For each donor, blood was drawn into six 4 mL blood collection tubes preserved with potassium EDTA or lithium heparin. The same donor blood was used for both anti-coagulants. Blood was drawn the same day as testing. The blood was no more than 4 hours old when used in the tests, and it was typically about 2 hours old. Prior to testing, the blood collection tubes were rotated using a single speed Nutator mixer (Clay Adams, BD Diagnostics).

For each donor, the hematocrit level was measured in triplicate by the spun microhematocrit method. The method used the Hemata STAT II system, which included a centrifuge and a built in automatic capillary tube reader.

Figure 6:
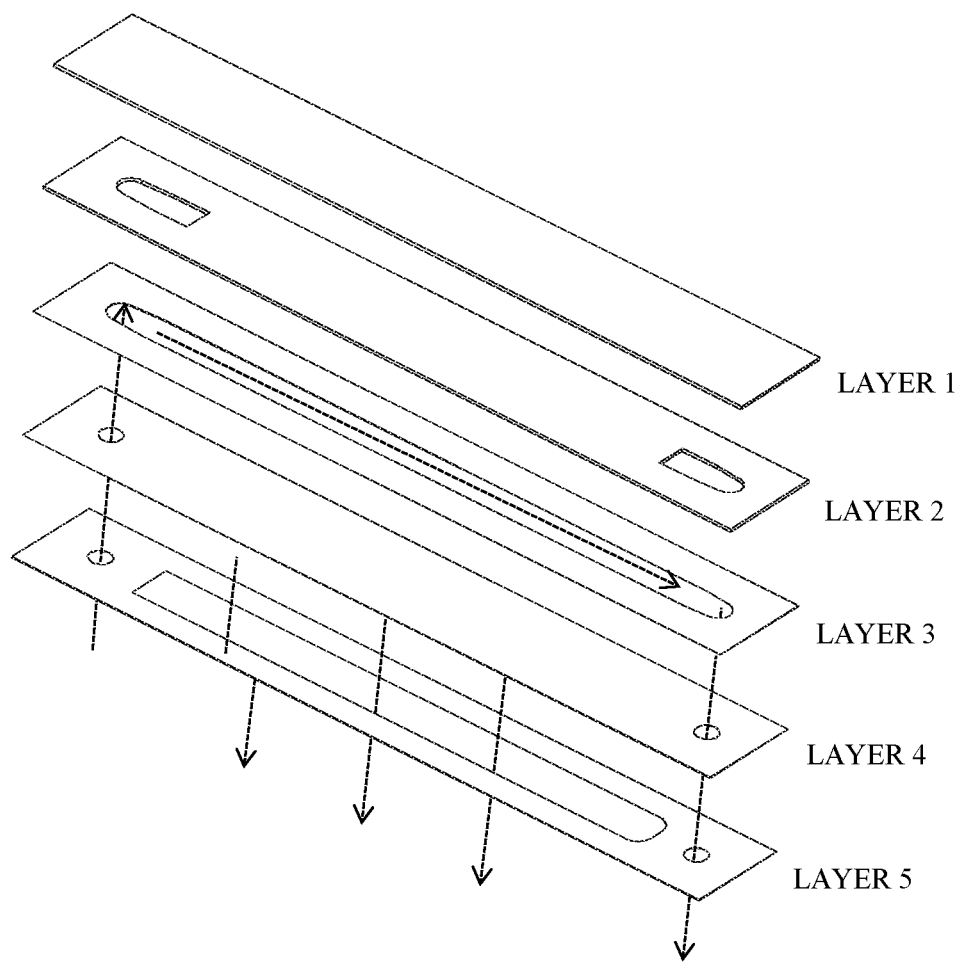
FIG. 6 is an expanded perspective view of a tangential flow filtration module described in the Examples, with arrows showing a flow path through the filtration module.

Filtration modules were fabricated for single sided mounting as shown in FIG. 6. The arrows show a flow path of a sample being filtered through an exemplary embodiment of the present disclosure. The layer components used to construct the filtration module were cut from sheet stock using a laser cutter or blade. The layer components were as follows:

Layer 1: 3M™ Polyester Diagnostic Single-Sided Tape 9794R

Layer 2: DuPont Teijin Melinex® ST730 Polyester film, 0.010 inch

Layer 3: 3M™ Double Coated Tape 9019, 0.0011 inch

Layer 4: Whatman Cyclopore™ polycarbonate filter element, 20 micron thickness

Layer 5: 3M™ Double Coated Tape 9019, 0.0011 inch

The filtration modules were manually assembled and pressed to ensure proper sealing between layers. For testing, the filtration modules were mounted to a filtration system as shown in FIG. 7. The filtration module was operated in a single pass process configuration.

The following procedure was used for operation of the filtration module. A filtration system was clamped onto a ring stand. The weight tare of the plasma collection tube was measured and recorded. The plasma collection tube was positioned on the underside of the filter module so as to receive the plasma. 2000 μL of blood was pipetted into an input reservoir. A septum was applied to the input reservoir. The pressure from the pump was verified and set to +4.0 +/− 0.1 PSIG. The pressure pump was connected to the input reservoir using a probe 212 to pierce and traverse the septum. The filtration commenced when pressure was applied and a timer started. The filtered plasma was collected into plasma collection tube until all blood passed through the filtration module at which point the timer was stopped. The plasma collection tube was weighed and the plasma volume yield and filtration time were calculated. The waste was collected and discarded.

Table 1 provides the results from a single donor with 41% hematocrit. A small difference was observed in the plasma recovery efficiency between the two anti-coagulants. The low surface area and the super thin layers promoted and resulted in high filtration efficiency.

TABLE 1

| | EDTA | Heparin |
|---|---|---|
| Plasma recovery efficiency | 39% | 37% |
| Time to filter 2000 uL, sec | 150 | 152 |
| Replicates | 3 | 2 |

Example 2

Comparison of Analyte Recovery Using Whatman Cyclopore™ and Whatman Nuclepore™ Filter Elements The analyte recovery was assessed by comparison of filtered plasma to centrifuged plasma from split specimens. The analyte concentration in filtered plasma was measured using two different filter elements.

Centrifuged plasma was prepared using a Beckman Coulter Allegra 6 R centrifuge. The blood was spun for 10 minutes at 2000 rpm.

Blood collection and preparation were the same as described in Example 1. The filtration module and filtration system were the same as described in Example 1, with the exception that a Whatman Nuclepore™ polycarbonate filter element, 9 micron thickness, was used in an embodiment for comparative purposes. The filtration module was operated in a single pass process configuration.

The analyte concentrations for hormones normally found in blood were measured using an Elecsys 2010. The results are shown in Table 2 and are expressed as a percentage of the concentration found from centrifuged blood. TSH is thyroid stimulating hormone and FSH is follicular stimulating hormone. The donor hematocrit was 42%. Each measurement was performed in triplicate.

TABLE 2

| | TSH | Free Thyroxine | Prolactine | FSH |
|---|---|---|---|---|
| Cyclopore ™ | 101.3% | 99.4% | 100.4% | 101.5% |
| Nuclepore ™ | 100.5% | 99.1% | 98.8% | 100.3% |

For hormones normally found in blood, such as TSH, free thyroxine, LH, prolactin, and FSH, no significant concentration difference was found between filtered and centrifuged plasma. The deviation from 100% recovery was due to analytical error in the method used to assay the plasma. The quality of the plasma from filtration was nearly the same as that for centrifuged plasma.

Example 3

Filtration Lysis by Measurement of Hemoglobin

An additional assessment of the quality of filtered plasma produced by the filtration module was made by measuring red blood cell lysis. The extent of red blood cell lysis was determined by measuring plasma hemoglobin concentration. A comparison was made to centrifuged plasma.

Blood collection and preparation were the same as described in Example 1. The filtration module and filtration system were the same as described in Example 1. The filtration module was operated in a single pass process configuration.

Plasma hemoglobin was assayed using the QuantiChrom Hemoglobin Assay kit (BioAssay Systems). The kit was based on the Triton/NaOH method where the hemoglobin is converted to a uniform colored end product. The procedure employed was according to the manufacturer's instructions. In summary, for each assay, 50 uL of sample was pipette into one well of an optically transparent 96 well plate. 200 uL of reagent was then pipette into each sample well. The plate was incubated at room temperature for 5 minutes. The optical density of each sample well was read at 400 nm using a plate reader (SpectraMax 384). In addition to the samples, a calibrator and a blank were run on each plate. A calibrator was provided with the kit. Water was used as the blank. The optical density for each sample was blank corrected and converted to hemoglobin concentration from the calibrator curve. All measurements were made in duplicate. The results are shown in Table 3. The plasma hemoglobin concentration units are mg/dl. Hct is hematocrit.

TABLE 3

| Donor | Hct | Hemoglobin by Filter | Hemoglobin by Centrifugation |
|---|---|---|---|
| 1 | 41% | 59 | 48 |
| 2 | 45% | 43 | 25 |
| 3 | 52% | 72 | 35 |

Across the donors and with hematocrit levels up to 52%, the hemoglobin concentration in filtered plasma was only slightly higher than that found in centrifuged plasma and well within acceptable levels. Thus, both methods achieved the desired low hemoglobin levels.

While various embodiments have been described, it is to be understood that variations and modifications may be resorted to as will be apparent to those skilled in the art. Such variations and modifications are to be considered within the purview and scope of the claims appended hereto.

What is claimed is:

1. A method for filtering a blood sample, the method comprising:
supplying the blood sample to a feeder channel of a filtration module wherein the filtration module comprises:
a feeder channel lid adjacent to a feeder channel laminating layer having a thickness of less than about 5 mil;
the feeder channel defined by the feeder channel lid and the feeder channel laminating layer;
a filter element having an inlet and a retentate outlet, the filter element adjacent to the feeder channel laminating layer and in fluid communication with the feeder channel, wherein the filter element inlet is adapted to receive the blood sample passing through the filtration module;
the filter element having:
a pore size of less than about 2 microns; and
a ratio of actual surface area to projected surface area of less than or equal to 5.0; and
a filtrate take-off layer adjacent to the filter element and having an inlet port, a retentate outlet port and a filtrate take-off port having a dead volume of less than about 10 µL, wherein the inlet port is adapted to receive the blood sample flowing into the filtration module and the retentate outlet port is adapted to carry a retentate out of the filtration module;
drawing the blood sample over the filter element of the filtration module in a single pass process configuration to provide the retentate and a plasma filtrate; and
discarding the retentate or further processing the plasma filtrate.

2. The method of claim 1, wherein the filtrate take-off port has a dead volume of less than or equal to 2.5 µL per mL of blood filtered.

3. The method of claim 1, wherein the filtrate take-off port has a dead volume of less than or equal to 2.9 µL per $cm^2$ of filtrate take-off port area.

4. A method for filtering a blood sample, the method comprising:
supplying the blood sample to a feeder channel of a filtration module, wherein the filtration module comprises:
a feeder channel lid adjacent to a feeder channel laminating layer having a thickness of less than about 5 mil;
the feeder channel defined by the feeder channel lid and the feeder channel laminating layer;
a filter element having an inlet and a retentate outlet, the filter element adjacent to the feeder channel laminating layer and in fluid communication with the feeder channel, wherein the filter element inlet is adapted to receive the blood sample passing through the filtration module;
the filter element having:
a pore size of less than about 2 microns; and
a filter element exposed area of less than or equal to 0.6 $cm^2$ per mL of filtered blood; and
a filtrate take-off layer adjacent to the filter element and having an inlet port, a retentate outlet port and a filtrate take-off port having a dead volume of less than about 10 µL, wherein the inlet port is adapted to receive the blood sample flowing into the filtration module and the retentate outlet port is adapted to carry a retentate out of the filtration module;
drawing the blood sample over the filter element of the filtration module in a single pass process configuration to provide the retentate and a plasma filtrate; and
discarding the retentate or further processing the plasma filtrate.

5. The method of claim 4, wherein the filtrate take-off port has a dead volume of less than or equal to 2.5 µL per mL of blood filtered.

6. The method of claim 4, wherein the filtrate take-off port has a dead volume of less than or equal to 2.9 µL per cm² of filtrate take-off port area.

7. A method for filtering a blood sample, the method comprising:
supplying the blood sample to a feeder channel of a filtration module wherein the filtration module comprises:
a support layer adjacent to a laminating element having one or more secondary channels adapted to fluidically communicate with an inlet port and an outlet port of a feeder channel lid;
the laminating element adjacent to the feeder channel lid;
the feeder channel lid adjacent to a feeder channel laminating layer;
a feeder channel defined by the feeder channel lid and the feeder channel laminating layer having a thickness of less than about 5 mil;
a filter element adjacent to the feeder channel laminating layer and in fluid communication with the feeder channel, the filter element having:
a pore size of less than about 2 microns; and
a ratio of actual surface area to projected surface area of less than or equal to 5.0;
a filtrate take-off layer adjacent to the filter element and having an inlet port, a retentate outlet port and a filtrate take-off port having a dead volume of less than about 10 µL, wherein the inlet port is adapted to receive the sample flowing into the filtration module and the retentate outlet port is adapted to carry a retentate out of the filtration module; and
drawing the blood sample over a filter element of the filtration module in a single pass process configuration to provide a retentate and a plasma filtrate, wherein the method comprises a plasma recovery efficiency of greater than about 15%.

8. The method of claim 7, wherein the filtrate take-off port has a dead volume of less than or equal to 2.5 µL per mL of blood filtered.

9. The method of claim 7, wherein the filtrate take-off port has a dead volume of less than or equal to 2.9 µL per cm² of filtrate take-off port area.

* * * * *